(12) United States Patent
Shirai

(10) Patent No.: US 6,546,783 B2
(45) Date of Patent: Apr. 15, 2003

(54) GAS SENSOR AND MANUFACTURING METHOD FOR THE SAME

(75) Inventor: Makato Shirai, Hekinan (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/879,069

(22) Filed: Jun. 13, 2001

(65) Prior Publication Data

US 2002/0017128 A1 Feb. 14, 2002

(30) Foreign Application Priority Data

Jun. 30, 2000 (JP) ........................................ 2000-198000
Apr. 20, 2001 (JP) ........................................ 2001-123119

(51) Int. Cl.⁷ .................. G01N 27/04; G01N 27/409; G01N 27/12
(52) U.S. Cl. ................... 73/31.05; 73/23.2; 73/23.31; 204/424; 204/426; 422/94
(58) Field of Search ............... 73/31.05, 23.31, 73/23.2; 204/424, 426; 422/94

(56) References Cited

U.S. PATENT DOCUMENTS

| | | | | |
|---|---|---|---|---|
| 4,225,842 A | * | 9/1980 | Schlesselman et al. | 338/34 |
| 4,236,138 A | * | 11/1980 | Segawa et al. | 338/34 |
| 4,308,518 A | * | 12/1981 | Hattori et al. | 338/34 |
| 4,883,643 A | * | 11/1989 | Nishio et al. | 422/94 |
| 5,329,806 A | * | 7/1994 | McClanahan et al. | 73/31.05 |
| 5,467,636 A | | 11/1995 | Thompson et al. | 73/23.31 |
| 5,490,412 A | * | 2/1996 | Duce et al. | 73/23.31 |
| 5,602,325 A | | 2/1997 | McClanahan et al. | 73/23.31 |
| 5,616,825 A | * | 4/1997 | Achey et al. | 73/23.31 |
| 5,739,414 A | | 4/1998 | Paulus et al. | 73/23.31 |
| 5,886,248 A | | 3/1999 | Paulus et al. | 73/23.31 |
| 6,202,472 B1 | * | 3/2001 | Wezurek et al. | 73/31.05 |
| 6,408,680 B2 | * | 6/2002 | Friese et al. | 73/23.31 |

FOREIGN PATENT DOCUMENTS

| | | |
|---|---|---|
| JP | 2800883 | 7/1998 |
| JP | 2855096 | 11/1998 |
| JP | 11-513113 | 11/1999 |

* cited by examiner

Primary Examiner—Hezron Williams
Assistant Examiner—David J. Wiggins
(74) Attorney, Agent, or Firm—Nixon & Vanderhye P.C.

(57) ABSTRACT

An air side cover is attached to a proximal end of a housing so as to confine an aerial atmosphere therein. A measured gas side cover is attached to a distal end of the housing so as to confine a measured gas atmosphere therein. A glass sealing material airtightly seals a clearance between an inner surface of an insulator and an outer surface of a sensing element. A contact interface of the glass sealing material protrudes toward a proximal end of the gas sensor compared with at least an adjacent portion of the remainder of the glass sealing material. By melting and hardening a glass pellet, the sensing element is airtightly fixed in the insulator.

2 Claims, 5 Drawing Sheets

GAS SENSOR AND MANUFACTURING METHOD FOR THE SAME

BACKGROUND OF THE INVENTION

The present invention relates to a gas sensor installed in an exhaust gas system of an internal combustion engine for a combustion control or else. Furthermore, the present invention relates to a method for manufacturing this gas sensor.

According to a conventional gas sensor, a sensing element is inserted into an insulator. The insulator is fixed in a housing. A measured gas side cover is attached to a distal end of the housing. An air side cover is attached to a proximal end of the housing. The clearance between the insulator and the housing is airtightly sealed. Similarly, the clearance between the sensing element and the insulator is airtightly sealed.

Presence of such an airtight sealing makes it possible to separate an inside space of the gas sensor into an aerial atmosphere and a measured gas atmosphere.

In general, the sensing element has a measured gas sensing electrode exposed to a measured gas and a reference gas sensing electrode exposed to the air serving as a reference gas. The sensing element produces a sensing signal representing a gas concentration in the measured gas based on an ion current or an electric potential produced between these electrodes. Hence, measurement of gas concentration cannot be performed accurately when separation between the aerial atmosphere and the measured gas atmosphere is insufficient.

Conventionally, powdered material, such as talc, and a sealing glass are layered between the sensing element and the insulator to airtightly separate the aerial atmosphere and the measured gas atmosphere.

For example, U.S. Pat. No. 5,602,325 discloses a plurality of solid-phase sintered glass layers and a plurality of steatite spacer layers which are alternately stacked in a ceramic sensor holder. A ceramic main body surrounds the alternately stacked glass layers and spacer layers. The ceramic main body extends to an outside housing. Furthermore, thin solid-phase sintered glass layers are interposed between the ceramic main body and each spacer layer.

Furthermore, U.S. Pat. Nos. 5,467,636 and 5,739,414 disclose a glass layer interposed between a first ceramic insulating body and a second ceramic insulating body. According to this prior art, the glass is subjected to a compressive stress acting in the radial direction (i.e., in the central direction) within an operating temperature zone.

However, securing airtightness by filling the powdered material, such as talc, requires checking many items to administrate the pressure and the filling amount of the powdered material. This in disadvantageous in costs.

Furthermore, the glass layer is generally formed through the processes of placing the powdered glass material to a predetermined position, heating the powdered glass material to melt it, and then cooling the molten glass until it is hardened. This makes it difficult to obtain a highly densified glass sealing material. Accordingly, it is difficult to maintain satisfactory airtightness for a gas sensor based on a sealing arrangement using the glass sealing material only.

SUMMARY OF THE INVENTION

In view of the above-described conventional problems, an object of the present invention is to provide a gas sensor having an arrangement capable of sealing the clearance between the insulator and the sensing element with the glass material only. Furthermore, the present invention provides a manufacturing method for this sensor.

In order to accomplish the above and other related objects, the present invention provides a gas sensor comprising a cylindrical insulator, a sensing element airtightly fixed in the insulator, and a cylindrical housing having an inside space for placing the insulator, with an air side cover attached to a proximal end of this housing so as to confine an aerial atmosphere therein, wherein a glass sealing material seals a clearance between an inner surface of the insulator and an outer surface of the sensing element, and a proximal end surface of the glass sealing material protrudes toward a proximal end of the gas sensor at a contact interface of the glass sealing material to the inner surface of the insulator and to the outer surface of the sensing element compared with at least an adjacent portion of the remainder.

The present invention is characterized in that the glass sealing material seals a clearance between the inner surface of the insulator and the outer surface of the sensing element. The proximal end surface of the glass sealing material protrudes toward the proximal end of the gas sensor at the contact interface of the glass sealing material to the inner surface of the insulator and to the outer surface of the sensing element compared with at least an adjacent portion of the remainder.

Next, function of the present invention will be explained.

According to the present invention, the proximal end surface of the glass sealing material protrudes toward the proximal end of the gas sensor at the contact interface of the glass sealing material to the inner surface of the insulator and to the outer surface of the sensing element compared with at least an adjacent portion of the remainder (refer to FIG. 2). This arrangement makes it possible to firmly fix the glass sealing material to the sensing element and to the insulator at the contact interface thereof, thereby maintaining improved airtightness.

Accordingly, it becomes possible to surely provide an airtight sealing for the clearance between the sensing element and the insulator by using a single glass sealing material such as a glass pellet, i.e., without using powdered material, and without requiring multistage filling processes of the sealing material, and further without requiring complicated check of numerous managing items.

According to the present invention, it becomes possible to provide a gas sensor capable of sealing the clearance between the insulator and the sensing element with the glass material only.

The glass sealing material is, for example, a material whose composition is expressed by $B_2O_3$—$ZnO$—$SiO_2$—$Al_2O_3$—$BaO$—$MgO$.

This material has an excellent sealing ability for the sensing element and the insulator. Thus, it becomes possible to ensure the reliable airtight sealing between the glass sealing material and the sensing element as well as between the glass sealing material and the insulator.

Furthermore, the present invention is applicable to a gas sensor incorporating a cup-shaped solid electrolytic sensing element as shown in FIG. 1, and also applicable to a gas sensor incorporating a multilayered sensing element.

Furthermore, the arrangement of the present invention is applicable to an oxygen sensor and to an air-fuel ratio sensor for an automotive internal combustion engine. Especially, when formed into a multilayered type, the arrangement of the present invention is preferably applicable to a NOx sensor, a CO sensor or the like.

Next, according to the present invention, it is preferable that a protruding portion of the proximal end surface corresponds to at least 98% of the contact interface which extends circumferentially along an entire periphery of the glass sealing material.

The expression "at least 98% of the contact interface" means that the contact interface between the glass sealing material and the inner surface of the insulator and the contact interface between the glass sealing material and the outer surface of the sensing element protrude by an amount of 98% or more in the circumferential direction.

When the protruding portion exceeds 98%, it becomes possible to surely provide an airtight sealing for the clearance between the sensing element and the insulator by using a single glass sealing material.

If the protruding portion is less than 98%, gas leakage may occur.

Needless to say, it is most preferable that the proximal end surface of the glass sealing material protrudes toward the proximal end of the gas sensor entirely along the circumferentially extending contact interface.

Next, the present invention provides a method for manufacturing a gas sensor comprising a cylindrical insulator, a sensing element airtightly fixed in the insulator, and a cylindrical housing having an inside space for placing the insulator, with an air side cover attached to a proximal end of the housing so as to confine an aerial atmosphere therein and a measured gas side cover attached to a distal end of the housing so as to confine a measured gas atmosphere therein, wherein a glass sealing material seals a clearance between an inner surface of the insulator and an outer surface of the sensing element, and a proximal end surface of the glass sealing material protrudes toward a proximal end of the gas sensor at a contact interface of the glass sealing material to the inner surface of the insulator and to the outer surface of the sensing element compared with at least an adjacent portion of the remainder.

The method of the present invention comprises the steps of preparing a cylindrical glass pellet having an outer shape fitting to the inner surface of the insulator and having a through-hole into which the sensing element is inserted, inserting the glass pellet into the insulator and placing the sensing element in the through-hole of the glass pellet, and melting the glass pellet and then hardening the molten glass to firmly seal the clearance between the inner surface of the insulator and the outer surface of the sensing element.

According to the manufacturing method of the present invention, the glass pellet configured into a predetermined shape is inserted into the insulator. Then, the sensing element is disposed in the through-hole of the glass pellet. Thereafter, the glass pellet is melted and hardened to firmly seal the clearance between the insulator and the sensing element.

Accordingly, compared with a conventional method for directly filling the clearance with powdered glass material etc. as a glass sealing material, it becomes possible to realize a highly densified glass sealing. Accordingly, it becomes easy to obtain a desired sealing in length as well as in volume, thereby realizing a reliable sealing.

Accordingly, it becomes possible to firmly fix the sensing element and the insulator at their interfaces so as to maintain excellent airtightness. Furthermore, it becomes possible to surely provide an airtight sealing for the clearance between the sensing element and the insulator by using a single glass sealing material only.

As described above, the present invention makes it possible to provide a manufacturing method for a gas sensor capable of sealing the clearance between the insulator and the sensing element with the glass material only.

Regarding the shape of the glass pellet, it is possible to form the glass pellet with side surfaces fitting to the inner surface of the insulator and to the outer surface of the sensing element. It is also possible to configure the glass pellet to have the through-hole beforehand so that the sensing element can be inserted into this through-hole.

It is also possible to use the glass pellet consisting of a plurality of parts.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENT

Figure 1:
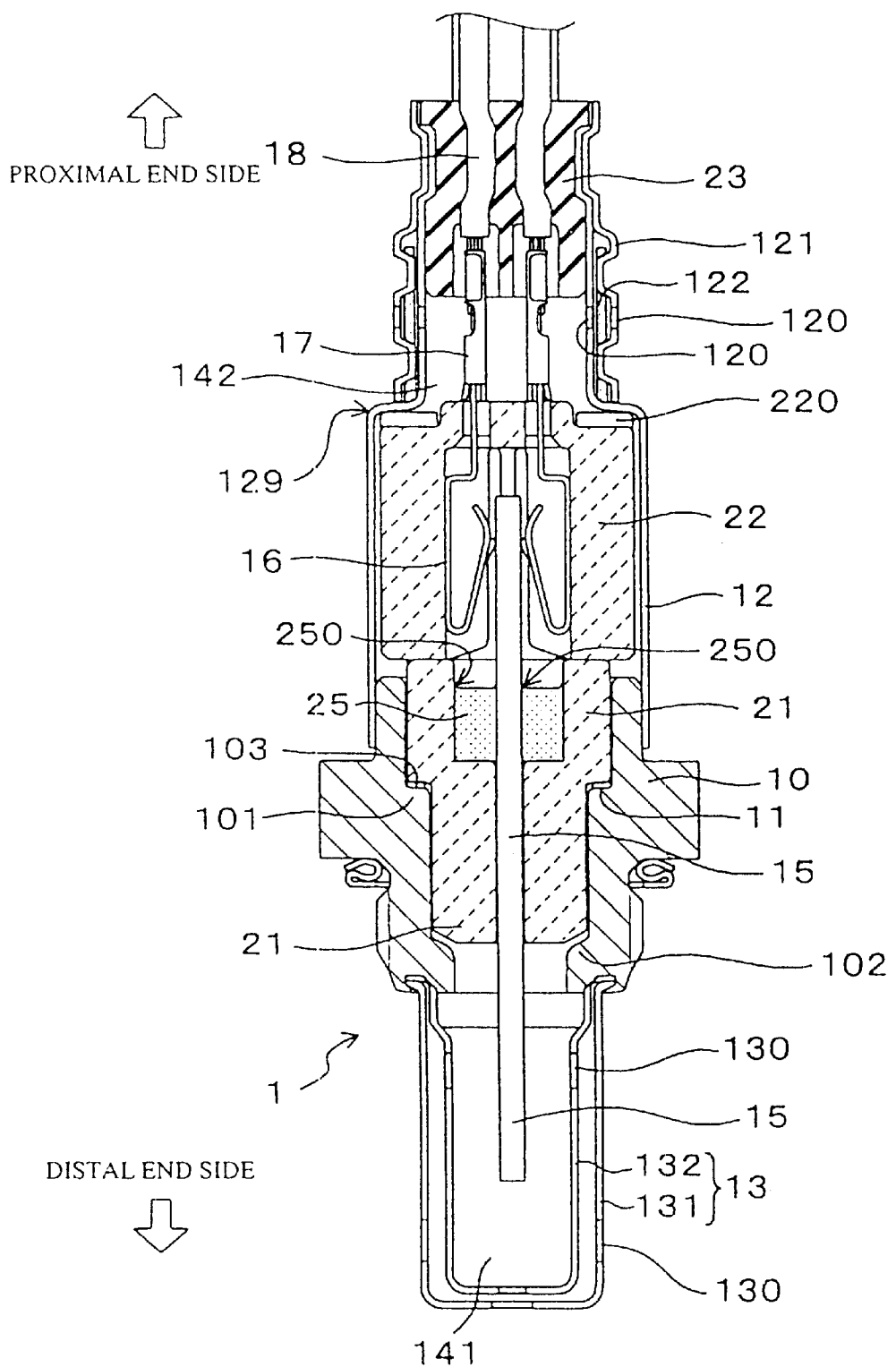
FIG. 1 is a vertical cross-sectional diagram showing a gas senor in accordance with a preferred embodiment of the present invention.

A preferred embodiment of the present invention will be explained hereinafter with reference to attached drawings. Identical parts are denoted by the same reference numerals throughout the drawings.

Hereinafter, a gas sensor according to a preferred embodiment of the present invention will be explained with reference to FIGS. 1 to 5.

In this explanation, a front side of a gas sensor to be exposed to a measured gas is referred to a distal end side and the opposite side is referred to a proximal end side.

As shown in FIG. 1, a gas sensor 1 of this embodiment comprises a cylindrical insulator 21, a sensing element 15 airtightly fixed in the insulator 21, and a cylindrical housing 10 having an inside space for placing the insulator 21. An air side cover 12 is attached to a proximal end of the housing 10 so as to confine an aerial atmosphere 142 therein. A measured gas side cover 13 is attached to a distal end of the housing 10 so as to confine a measured gas atmosphere 141 therein.

Figure 2:
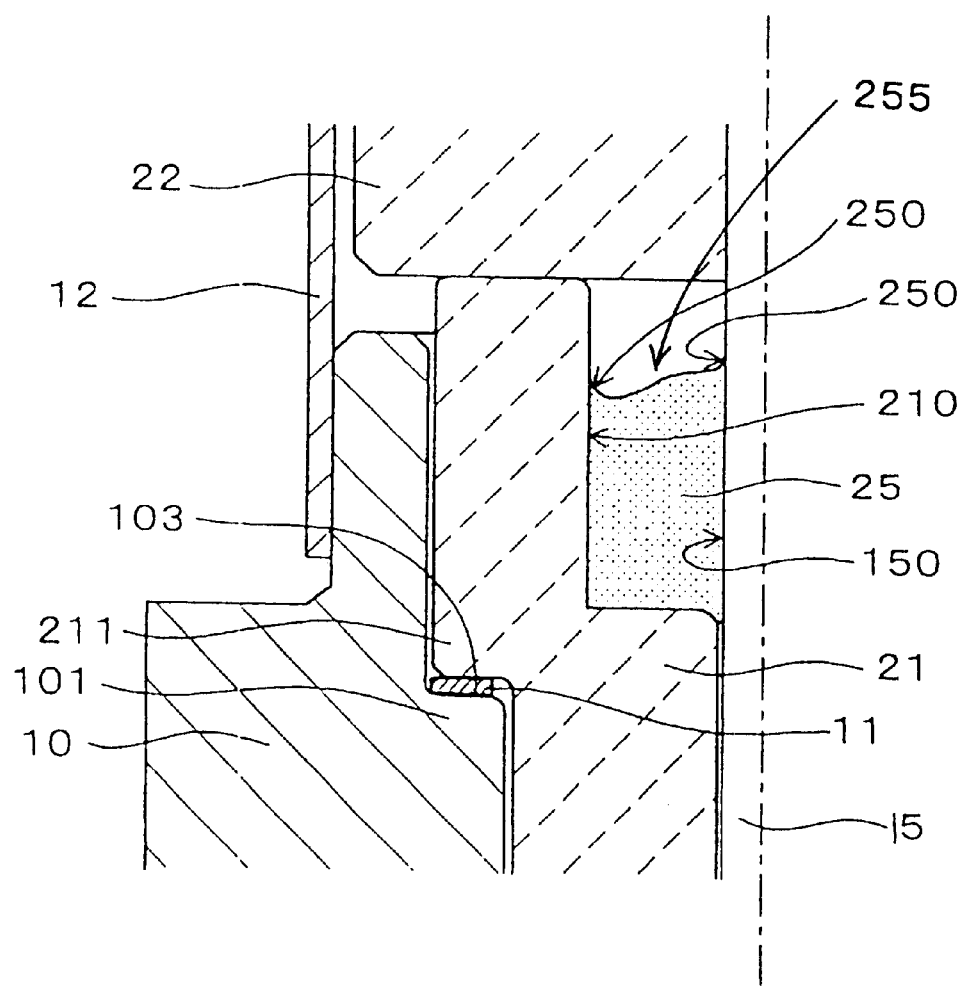
FIG. 2 is an enlarged cross-sectional diagram showing an essential arrangement of the gas sensor in accordance with the preferred embodiment of the present invention.

As shown in FIG. 2, a glass sealing material 25 airtightly seals a clearance between an inner surface 210 of the insulator 21 and an outer surface 150 of the sensing element 15. A proximal end surface 255 of the glass sealing material 25 protrudes toward a proximal end of the gas sensor 1 at a contact interface 250 of the glass sealing material 25 to the inner surface 210 of the insulator 21 and at a contact interface 250 of the glass sealing material 25 to the outer surface 150 of the sensing element 15 compared with at least an adjacent portion of the remainder.

Hereinafter, this embodiment will be explained in more detail.

The gas sensor 1 of this embodiment is installed in an exhaust system of an automotive internal combustion engine and is used for an air-fuel ratio control of the internal combustion engine.

As shown in FIG. 1, in the gas sensor 1, the measured gas side cover 13 attached at the distal end of the housing 10 consists of an outer cover 131 and an inner cover 132 cooperatively constituting a double-layer construction. Both of the outer cover 131 and the inner cover 132 are provided with holes 130 through which the measured gas is introduced into the measured gas side cover 13 so as to form the measured gas atmosphere 141.

The air side cover 12 is provided at the proximal end of the housing 10. An outer cover 121 is overlapped with an outer surface of the air side cover 12 at a proximal end thereof via a water-repellent filter 122. The overlapped portions of the air side cover 12 and the outer cover 121 are provided with holes 120 for introducing air into the air side cover 12 via the water-repellent filter 122.

The air side cover 12 has a smaller-diameter portion at its proximal end and a larger-diameter portion at its distal end which are integrally and continuously formed via a stepped portion 129.

The air introduced in the air side cover 12 through the air-introducing holes 120 forms the aerial atmosphere 142 of the gas sensor 1.

As shown in FIGS. 1 and 2, the housing 10 is configured into a cylindrical shape and has two protrusions 101 and 102 protruding radially inward from an inner surface thereof.

The protrusion 101, positioned at the proximal end side, has a receiving surface 103 which supports a tapered portion 211 provided at an outer surface of the insulator 21.

The insulator 21 is made of alumina ceramic having fineness of 98%.

The tapered portion 211 is supported on the receiving surface 103 via an annular metallic packing 11 (refer to FIG. 2). The metallic packing 11 is made of a nickel member having fineness of 99%.

The inside space of the gas sensor 1 is airtightly separated into the aerial atmosphere and the measured gas atmosphere at the portion where the metallic packing 11 is disposed.

An air side insulator 22 is disposed at a proximal end of the insulator 21. An annular disc spring 220 is disposed between the air side insulator 22 and the stepped portion 129 of the air side cover 12.

A total of four leads 16 are disposed in an inside space of the air side insulator 22 so as to be electrically conductive with the sensing element 15.

The sensing element 15, used for detecting an oxygen concentration, has a multilayer body equipped with a built-in heater. Although not shown in the drawing, the sensing element 15 has two sensor electrodes for taking out a sensor output signal, two power electrodes for supplying electric power to the heater, and a total of four electrode terminals taken out of the sensor body.

The four leads 16 are disposed so as to be brought into contact with these four electrode terminals respectively.

A proximal end of each lead 16 is connected to a lead 18 via a connector 17 at an outside of the air side insulator 22. The lead 18 extends out of the gas sensor 1 through an elastic insulating member 23 disposed at a proximal end side of the air side cover 12.

As shown in FIG. 2, the sensing element 15 is placed in an inside space of the insulator 21. The glass sealing material 25 airtightly seals the clearance between the sensing element 15 and the insulator 21. A proximal end surface 255 of the glass sealing material 25 is raised at a circumferential edge of the glass sealing material 25, i.e., at the contact interface 250 to the sensing element 15 and to the insulator 21.

The contact interface 250 is annular. More specifically, the annular contact interface 250 between the glass sealing material 25 and the insulator 21 has a circular cross section. The annular contact interface 250 between the glass sealing material 25 and the sensing element 15 has a polygonal cross section. According to this embodiment, both of the circular contact interface 250 and the polygonal contact interface 250 are entirely raised along their circumferential peripheries.

Furthermore, the glass sealing material 25 contains 21% (weight percentage) $B_2O_3$, 34.6% ZnO, 12.2% $SiO_2$, 4.9% $Al_2O_3$, 14.2% BaO, and 12.7% MgO.

According to this embodiment, seal fixation between the sensing element 15 and the insulator 21 of the gas sensor 1 is performed in the following manner.

Figure 3:
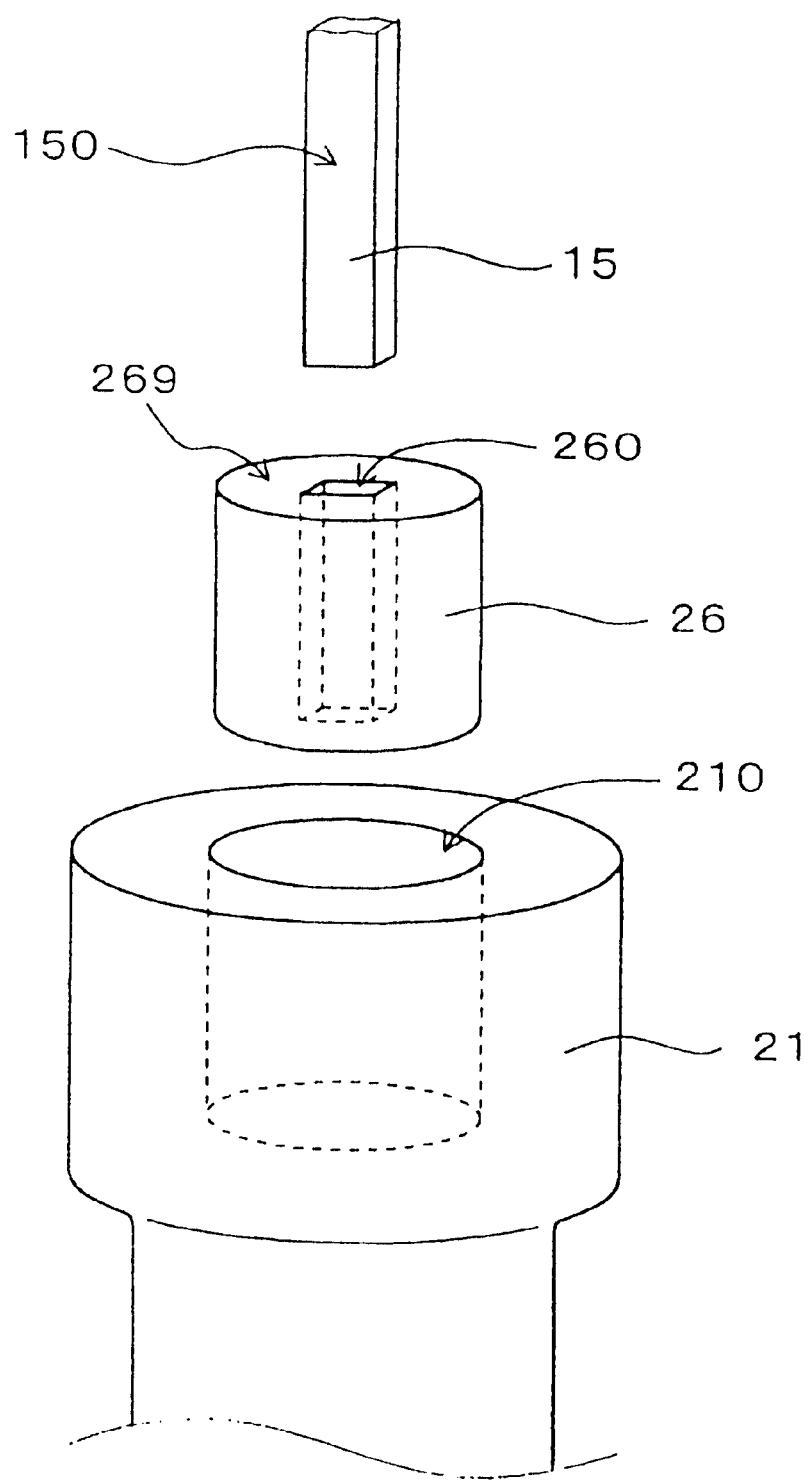
FIG. 3 is a diagram showing the assembling of a sensing element, an insulator, and a glass pellet in accordance with the preferred embodiment of the present invention.

As shown in FIG. 3, a cylindrical glass pellet 26 is prepared in addition to the insulator 21 and the sensing element 15. The cylindrical glass pellet 26 has an outer shape fitting to the inner surface 210 of the insulator 21 and has a through-hole 260 into which the sensing element 15 is inserted. A proximal end surface 269 of the glass pellet 26 is flat.

First, the sensing element 15 is inserted into the glass pellet 26. Next, the glass pellet 26 is inserted into the insulator 21. The order of assembling the sensing element 15, the glass pellet 26, and the insulator 21 is not limited to the above-described one and therefore can be inversed.

Thereafter, these three members are integrally heated in a furnace at the temperature of 800° C. to 950° C. for 30 minutes to five hours to melt the glass pellet 26 and then naturally cooled down to harden the molten glass.

When the glass pellet 26 melts, the molten glass can be raised at the contact interface 250 to the sensing element 15 and to the insulator 21 due to surface tension. Therefore, after being naturally cooled down, the glass material protrudes at the contact interface 250 toward the proximal end of the gas sensor 1 while the remainder of the glass material remains substantially flat as shown in FIGS. 1 and 2. Thus, the clearance is airtightly filled with the glass material so as to provide improved sealing.

Then, the integrated assembly of the sensing element 15 and the insulator 21 is placed in the housing 10 via a metallic packing 11, thereby constituting the gas sensor 1.

Next, functions and effects of this embodiment will be explained.

According to this embodiment, as shown in FIG. 2, the proximal end surface 255 of the glass sealing material 25 protrudes toward the proximal end of the gas sensor 1 at the contact interface 250 of the glass sealing material 25 to the inner surface 210 of the insulator 21 and to the outer surface 150 of the sensing element 15 compared with at least an adjacent portion of the remainder. Thus, the interface between the glass sealing material 25 and the sensing element 15 as well as the interface between the glass sealing material 25 and the insulator 21 are firmly fixed so as to provide excellent airtightness.

Furthermore, according to the method of this embodiment, as shown in FIG. 3, the glass pellet 26 configured into a predetermined shape is inserted into the insulator 21. Then, the sensing element 15 is disposed in the through-hole 260 of the glass pellet 26. Thereafter, the glass pellet 26 is melted and hardened to firmly seal the clearance between the insulator 21 and the sensing element 15.

Accordingly, compared with a conventional method for filling the clearance with powdered glass material etc. as a glass sealing material, it becomes possible to realize an excellent sealing using the highly densified glass sealing material 25.

Accordingly, it becomes possible to surely provide an airtight sealing for the clearance between the sensing element and the insulator by using a single glass sealing material such as a glass pellet, i.e., without using powdered material, and without requiring multistage filling processes of the sealing material, and further without requiring check of numerous managing items.

According to this embodiment, it becomes possible to provide a gas sensor capable of sealing the clearance between the insulator and the sensing element with the glass material only. Furthermore, it becomes possible to provide a method for manufacturing the gas sensor.

The following tables 1 to 6 show the components of other glass sealing materials preferable used for the gas sensor in accordance with the present invention. In each table, the content (wt %) represents a value expressed in terms of oxide.

TABLE 1

| component | content (wt %) |
|---|---|
| $B_2O_3$ | 21.0 ± 3 |
| ZnO | 34.6 ± 3 |
| $SiO_2$ | 12.6 ± 3 |
| $Al_2O_3$ | 4.9 ± 3 |
| BaO | 14.2 ± 3 |
| MgO | 12.7 ± 2 |

TABLE 2

| component | content (wt %) |
|---|---|
| $B_2O_3$ | 21.0 ± 3 |
| ZnO | 32.0 ± 3 |
| $SiO_2$ | 19.0 ± 3 |
| BaO | 12.0 ± 3 |
| MgO | 16.0 ± 3 |

TABLE 3

| component | content (wt %) |
|---|---|
| $B_2O_3$ | 24.0 ± 3 |
| ZnO | 45.0 ± 5 |
| $SiO_2$ | 14.0 ± 3 |
| BaO | 7.5 ± 3 |
| MgO | 7.5 ± 3 |

TABLE 4

| component | content (wt %) |
|---|---|
| $B_2O_3$ | 24.3 ± 3 |
| ZnO | 57.5 ± 5 |
| $SiO_2$ | 11.0 ± 3 |
| BaO | 7.5 ± 3 |

TABLE 5

| component | content (wt %) |
|---|---|
| $B_2O_3$ | 22.6 ± 3 |
| ZnO | 34.5 ± 5 |
| $SiO_2$ | 12.8 ± 3 |
| BaO | 11.5 ± 3 |
| MgO | 18.6 ± 3 |

TABLE 6

| component | content (wt %) |
|---|---|
| $B_2O_3$ | 19.0 ± 3 |
| ZnO | 30.4 ± 5 |
| $SiO_2$ | 16.0 ± 3 |
| $Al_2O_3$ | 5.0 ± 3 |
| BaO | 20.0 ± 3 |
| CaO | 9.6 ± 3 |

To evaluate the present invention, a gas leakage amount was measured in relation to a raised amount of the contact interface 250 between the inner surface 210 of the insulator and the glass sealing material 25.

Figure 4A:
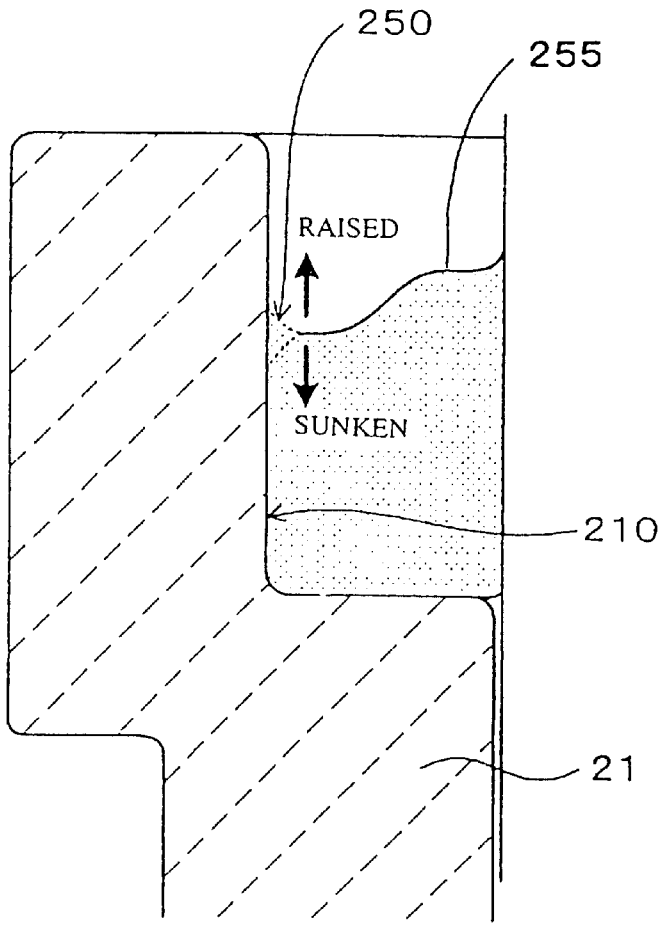
FIG. 4A is an enlarged cross-sectional diagram showing a contact interface between an inner surface of the insulator and a glass sealing material in accordance with the preferred embodiment of the present invention.

More specifically, many gas sensors were prepared and classified into two groups according to the condition (i.e., raised or sunken condition as shown in FIG. 4A) of the contact interface 250 between the inner surface 210 of the insulator 21 and the glass sealing material 25 in each gas sensor.

The gas leakage amount was measured in the following manner.

Figure 5:
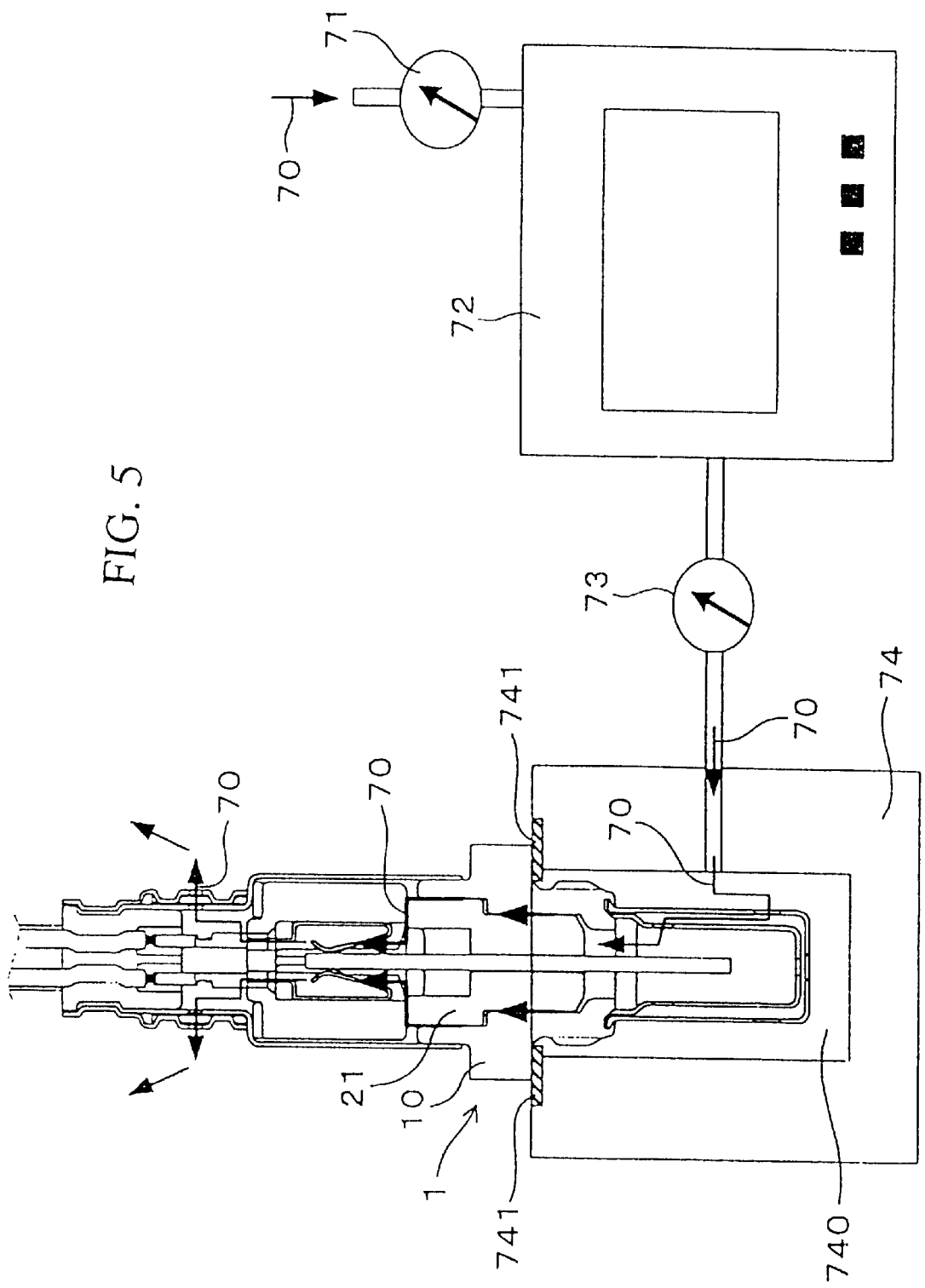
FIG. 5 is a diagram showing an apparatus measuring the gas leakage amount of a tested gas sensor in accordance with the preferred embodiment of the present invention.

Each gas sensor was installed in an apparatus shown in FIG. 5 to measure a gas leakage amount at the air side and at the measured gas side. The apparatus shown in FIG. 5 comprises a gas leakage amount measuring device 72 equipped with a valve 71 controlling an air supply amount, a gas sensor attachment jig 74, and a valve 73 provided in a pipe connecting the gas leakage amount measuring device 72 and the gas sensor attachment jig 74.

Hereinafter, the measuring method will be explained in more detail.

First, the gas sensor 1 is installed in the sensor attachment jig 74. The air side and the measured gas side are airtightly separated. In this condition, both of the valves 71 and 73 are opened to supply air into an air reservoir 740 of the attachment jig 74. A rubber packing 741 is provided to seal the clearance between the housing 10 of the gas sensor 1 and the attachment jig 74.

If the sealing between the insulator 21 and the glass sealing member 25 is insufficient, air will leak from the clearance between them as shown by the arrows in the drawing. The pressure in the air reservoir 740 decreases with elapsed time.

Accordingly, this apparatus is used to supply a predetermined amount of air (4 atm) to the air reservoir 740 and then to measure a pressure drop in the air reservoir 740 after the passage of 10 seconds. The gas leakage amount ($cm^3$) can be known from the measured pressure drop. It is however noted that a preliminary test should be done beforehand to confirm no presence of gas leakage from other portions.

Figure 4B:
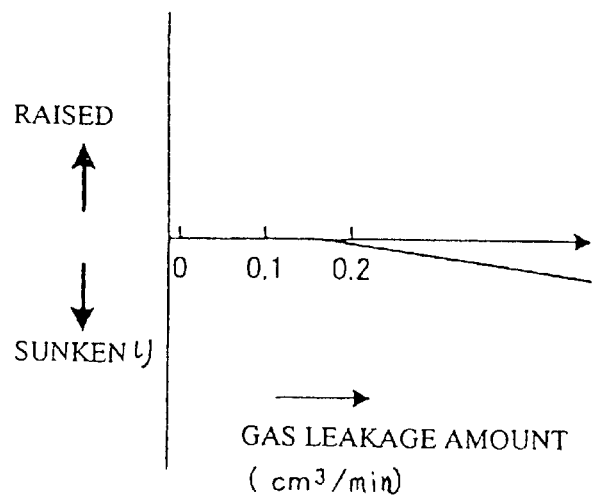
FIG. 4B is a graph showing a raised amount of the contact interface between the inner surface of the insulator and the glass sealing material in relation to gas leakage amount in accordance with the preferred embodiment of the present invention.

FIG. 4B shows the result of measurement.

From FIG. 4B, it is understood that any gas leakage may occur when the raised amount is reduced to 0.

The raised amount can be precisely measured based on observation of the contact interface 250 on a scanning electron microscopic view. The measurement data of this embodiment are thus obtained through the scanning electron microscopic observation.

Although this embodiment discloses the measurement result for the contact interface 250 between the insulator 21 and the glass sealing material 25, similar result was obtained when the gas leakage amount was measured for the contact interface 250 between the sensing element 15 and the glass sealing material 25.

Considering the evaluation test result, it is preferable that a protruding portion of the proximal end surface 255 of the glass sealing material 25 extends in a circumferential region corresponding to at least 98% of the contact interface which extends circumferentially along an entire periphery of the glass sealing material 25.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensor comprising a cylindrical insulator, a sensing element airtightly fixed in said insulator, and a cylindrical housing having an inside space for placing said insulator, with an air side cover attached to a proximal end of said housing so as to confine an aerial atmosphere therein, wherein a glass sealing material seals a clearance between an inner surface of said insulator and an outer surface of said sensing element, and a proximal end surface of said glass sealing material protrudes toward a proximal end of said gas sensor at a contact interface of said glass sealing material to the inner surface of said insulator and to the outer surface of said sensing element compared with at least an adjacent portion of the remainder.

2. The gas sensor in accordance with claim 1, wherein a protruding portion of said proximal end surface corresponds to at least 98% of said contact interface which extends circumferentially along an entire periphery of said glass sealing material.

\* \* \* \* \*